US009752430B2

(12) United States Patent
Mostowfi et al.

(10) Patent No.: US 9,752,430 B2
(45) Date of Patent: Sep. 5, 2017

(54) APPARATUS AND METHOD FOR MEASURING PHASE BEHAVIOR

(75) Inventors: Farshid Mostowfi, Edmonton (CA); Shahnawaz Hossain Molla, Edmonton (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 523 days.

(21) Appl. No.: 14/346,965

(22) PCT Filed: Jul. 3, 2012

(86) PCT No.: PCT/US2012/045379
§ 371 (c)(1),
(2), (4) Date: May 15, 2014

(87) PCT Pub. No.: WO2013/070283
PCT Pub. Date: May 16, 2013

(65) Prior Publication Data
US 2014/0238122 A1    Aug. 28, 2014

Related U.S. Application Data

(60) Provisional application No. 61/557,019, filed on Nov. 8, 2011.

(51) Int. Cl.
| G01N 21/05 | (2006.01) |
| E21B 49/00 | (2006.01) |
| G01N 21/55 | (2014.01) |
| G01N 35/10 | (2006.01) |
| B01L 3/00 | (2006.01) |

(Continued)

(52) U.S. Cl.
CPC ............ *E21B 49/00* (2013.01); *B01L 3/5027* (2013.01); *G01N 21/05* (2013.01); *G01N 21/55* (2013.01); *G01N 33/2823* (2013.01); *G01N 35/1097* (2013.01); *B01L 2200/0673* (2013.01); *B01L 2300/0816* (2013.01); *B01L 2300/0883* (2013.01); *B01L 2300/14* (2013.01); *B01L 2400/0406* (2013.01); *B01L 2400/049* (2013.01); *B81B 2207/03* (2013.01); *G01N 2021/0346* (2013.01)

(58) Field of Classification Search
CPC ...... E21B 49/00; F04B 49/06; G01N 33/2841
USPC ........................................................ 73/19.1
See application file for complete search history.

(56) References Cited

U.S. PATENT DOCUMENTS

| 4,395,902 A | 8/1983 | Espenscheid et al. |
| 7,000,452 B2 | 2/2006 | Bonne et al. |

(Continued)

FOREIGN PATENT DOCUMENTS

| EP | 2 008 716 A1 | 12/2008 |
| WO | 01/63270 A1 | 8/2001 |

(Continued)

*Primary Examiner* — Peter Macchiarolo
*Assistant Examiner* — Alexander Mercado

(57) ABSTRACT

An apparatus for measuring phase behavior of a reservoir fluid comprises a first sample container and a second sample container in fluid communication with a microfluidic device defining a microchannel. A first pump and a second pump are operably associated with the sample containers and the microfluidic device to fill the microchannel with a reservoir fluid and to maintain a predetermined pressure of reservoir fluid within the microchannel.

20 Claims, 7 Drawing Sheets

(51) Int. Cl.
*G01N 33/28* (2006.01)
*G01N 21/03* (2006.01)

(56) References Cited

U.S. PATENT DOCUMENTS

| | | | |
|---|---|---|---|
| 8,340,913 | B2 | 12/2012 | Mostowfi et al. |
| 8,485,026 | B2 | 7/2013 | Mostowfi |
| 2002/0166592 | A1 | 11/2002 | Liu et al. |
| 2006/0193730 | A1* | 8/2006 | Rosenstein ........... B01L 3/0293 417/53 |
| 2009/0326827 | A1 | 12/2009 | Mostowfi et al. |
| 2010/0017135 | A1 | 1/2010 | Mostowfi |
| 2011/0253222 | A1 | 10/2011 | Arai |

FOREIGN PATENT DOCUMENTS

| | | |
|---|---|---|
| WO | 2009/082674 A1 | 7/2009 |
| WO | 2011/013111 A2 | 2/2011 |

* cited by examiner

APPARATUS AND METHOD FOR MEASURING PHASE BEHAVIOR

CROSS-REFERENCE TO RELATED APPLICATIONS

This application claims priority from U.S. Provisional Application 61/557,019, filed Nov. 8, 2011, the disclosure of which is incorporated by reference herein in its entirety.

BACKGROUND

Pressure-volume-temperature measurements are used in predicting complicated thermo-physical behavior of a fluid, such as, but not limited to, the thermo-physical behavior of reservoir fluids. For example, pressure-volume-temperature measurements are used in developing thermodynamic models describing the state of a fluid at different temperature and pressure conditions.

Conventional pressure-volume-temperature measurements are typically performed in a pressurized cell with a window for visual observation of a sample being characterized. In such systems, the pressure on the sample is maintained by controlling a piston inside the cell. The cell is typically disposed inside an oven to accurately control the temperature of the sample. Volumes of liquid and gas phases inside the cell are monitored as a function of pressure and temperature to study the phase behavior of the sample. Conventional pressure-volume-temperature measurements, however, may take up to several weeks to complete due to the lengths of time required to achieve temperature and pressure equilibrium within the cell. Moreover, conventional pressure-volume-temperature measurements typically require significant sample volumes, which are typically transported to the laboratory in pressurized containers to preserve the condition of the sample.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, the disclosed subject matter of the application provides an apparatus for measuring phase behavior of a reservoir fluid. The apparatus, in one embodiment, comprises a microfluidic device defining an entrance passageway, an exit passageway, and a microchannel in fluid communication with the entrance passageway and the exit passageway. The apparatus further comprises a first sample container in fluid communication with the entrance passageway of the microfluidic device and a first pump operably associated with the first sample container. The first pump is configured to urge the reservoir fluid, disposed in the first sample container, into the entrance of the microfluidic device, through the microfluidic device, and into a second sample container in fluid communication with the exit passageway of the microfluidic device. The second sample container is also selectively in fluid communication with the entrance passageway of the microfluidic device and a second pump is operably associated with the second sample container. The second pump is operable to maintain a desired pressure within the microchannel of the microfluidic device.

In another aspect, an apparatus for measuring phase behavior of a reservoir fluid includes, in one embodiment, a microfluidic device defining an entrance passageway, an exit passageway, and a microchannel in fluid communication with the entrance passageway and the exit passageway. The apparatus further includes a first sample container in fluid communication with the entrance passageway of the microfluidic device and a first pump operably associated with the first sample container. The first pump is configured to urge the reservoir fluid, disposed in the first sample container, into the entrance of the microfluidic device, through the microfluidic device, and into a second sample container in fluid communication with the exit passageway of the microfluidic device. The apparatus further comprises an inlet pressure sensor operably associated with the entrance passageway of the microfluidic device. The second sample container is also selectively in fluid communication with the entrance passageway of the microfluidic device. The apparatus further includes a second pump operably associated with the second sample container. The apparatus further includes an outlet pressure sensor operably associated with the exit passageway of the microfluidic device, a camera operably associated with the microfluidic device, and a computer operably associated with the first pump, the inlet pressure sensor, the second pump, and the outlet pressure sensor. The computer is configured to operate the first pump and the second pump to provide a desired pressure drop across the microchannel of the microfluidic device.

In yet another aspect, a method for measuring phase behavior of a reservoir fluid includes injecting a reservoir fluid into a microchannel of a microfluidic device at a pressure resulting in a substantially single phase in the reservoir fluid and lowering the pressure of the reservoir fluid in the microchannel until a second phase forms in the reservoir fluid. The method further comprises determining a distribution of the phases of the reservoir fluid in the microchannel.

BRIEF DESCRIPTION OF THE DRAWINGS

Embodiments of the disclosed subject matter of the application are described with reference to the following figures. The same numbers are used throughout the figures to reference like features and components.

Figure 1:
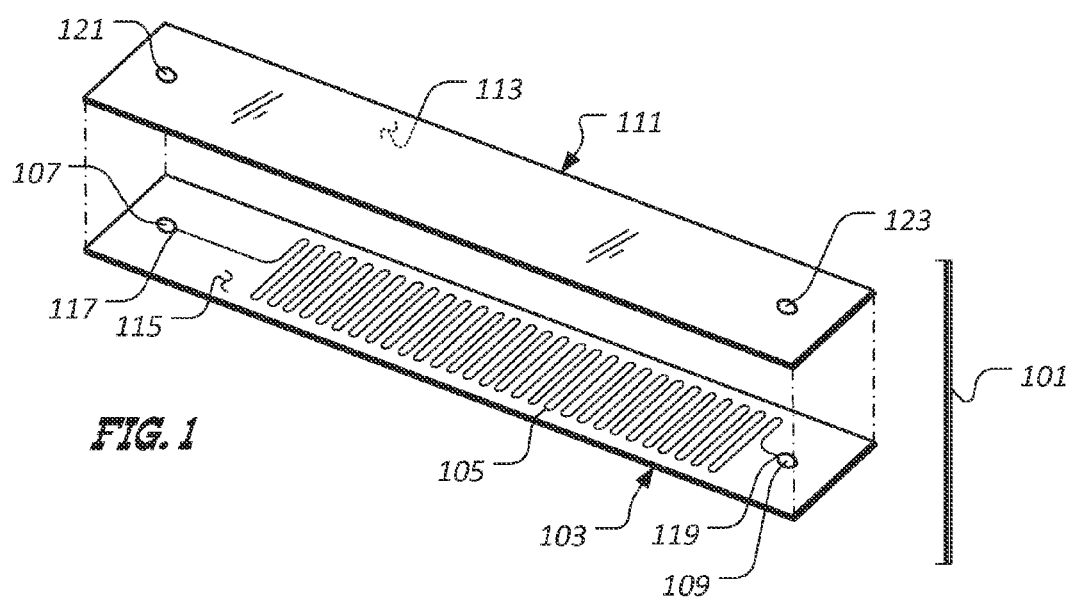
FIG. 1 is a stylized, exploded, perspective view of an illustrative embodiment of a microfluidic device.

While the disclosed subject matter of the application is susceptible to various modifications and alternative forms, specific embodiments thereof have been shown by way of example in the drawings and are herein described in detail.

It should be understood, however, that the description herein of specific embodiments is not intended to limit the disclosed subject matter of the application to the particular forms disclosed, but on the contrary, the intention is to cover all modifications, equivalents, and alternatives falling within the scope of the disclosed subject matter of the application as defined by the appended claims.

DETAILED DESCRIPTION

Illustrative embodiments of the disclosed subject matter of the application are described below. In the interest of clarity, not all features of an actual implementation are described in this specification. It will, of course, be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

The disclosed subject matter of the application relates to an apparatus and method for determining thermo-physical properties of a fluid. Generally, a sample is injected as a single phase into a channel of a microfluidic device. A substantially constant pressure is maintained in the channel, i.e., a hydrostatic pressure is maintained in the channel. The pressure in the channel is reduced in steps to determine at least one of a saturation pressure and a phase volume distribution ratio.

Figure 2:
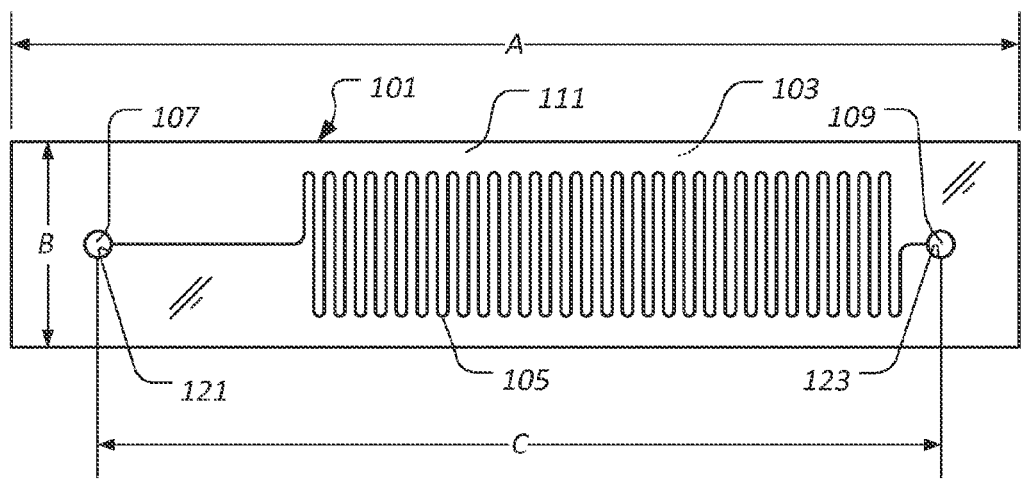
FIG. 2 is a top, plan view of the microfluidic device embodiment of FIG. 1.

FIGS. 1 and 2 depict views of an illustrative embodiment of a microfluidic device 101. In particular, FIG. 1 depicts a stylized, exploded, perspective view of microfluidic device 101 and FIG. 2 depicts a top, plan view of microfluidic device 101. In the illustrated embodiment, microfluidic device 101 comprises a first substrate 103 defining a microchannel 105, an entrance well 107 and an exit well 109. Microchannel 105 extends between and is in fluid communication with entrance well 107 and exit well 109. Microchannel 105 forms a serpentine pattern in first substrate 103, thus allowing microchannel 105 to extend a significant length but occupy a relatively small area. It should be noted, however, that microchannel 105 may take on forms different than that depicted in FIGS. 1 and 2 and that such embodiments are encompassed within the disclosed subject matter of the application. In one embodiment, microchannel 105 exhibits a length of about one or more meters, a width of about 100 micrometers, and a depth of about 50 micrometers, although the disclosed subject matter of the application includes other dimensions for microchannel 105. Microfluidic device 101 further comprises a second substrate 111 having a lower surface 113 that is bonded to an upper surface 115 of first substrate 103. When second substrate 111 is bonded to first substrate 103, microchannel 105 is substantially sealed except for an inlet 117 at entrance well 107 and an outlet 119 at exit well 109. Second substrate 111 defines an entrance passageway 121 and an exit passageway 123 therethrough, which are in fluid communication with entrance well 107 and exit well 109, respectively, of first substrate 103.

In the embodiment depicted in FIGS. 1 and 2, first substrate 103 is made from silicon, a silicon wafer, glass, or the like, and second substrate 111 is made from glass, such as borosilicate glass, although the disclosed subject matter of the application includes other materials for first substrate 103 and second substrate 111. Exemplary borosilicate glasses are manufactured by Schott North America, Inc. of Elmsford, N.Y., USA, and by Corning Incorporated of Corning, N.Y., USA. Microchannel 105, entrance well 107, and exit well 109 are, in one embodiment, first patterned onto first substrate 103 using a photolithography technique and then etched into first substrate 103 using a deep reactive ion etching technique. In one embodiment, entrance passageway 121 and exit passageway 123 are generated in second substrate 111 using a water jet or abrasive water jet technique. It should be noted, however, that the scope of the disclosed subject matter of the application includes other techniques for generating microchannel 105, entrance well 107, exit well 109, entrance passageway 121, and exit passageway 123. First substrate 103 and second substrate 111 are, in one embodiment, fused to one another using an anodic bonding method after careful cleaning of the bonding surfaces of substrates 103 and 111, e.g., lower surface 113 of second substrate 111 and upper surface 115 of first substrate 103. The disclosed subject matter of the application includes microfluidic device 101 having any suitable size and/or shape needed for a particular implementation. In one embodiment, as shown in FIG. 2, microfluidic device 101 exhibits an overall length A of about 80 millimeters and an overall width B of about 15 millimeters. In such an embodiment, passageways 121 and 123 are spaced apart a distance C of about 72 millimeters, although other arrangements are contemplated by the disclosed subject matter of the application.

Figure 3:
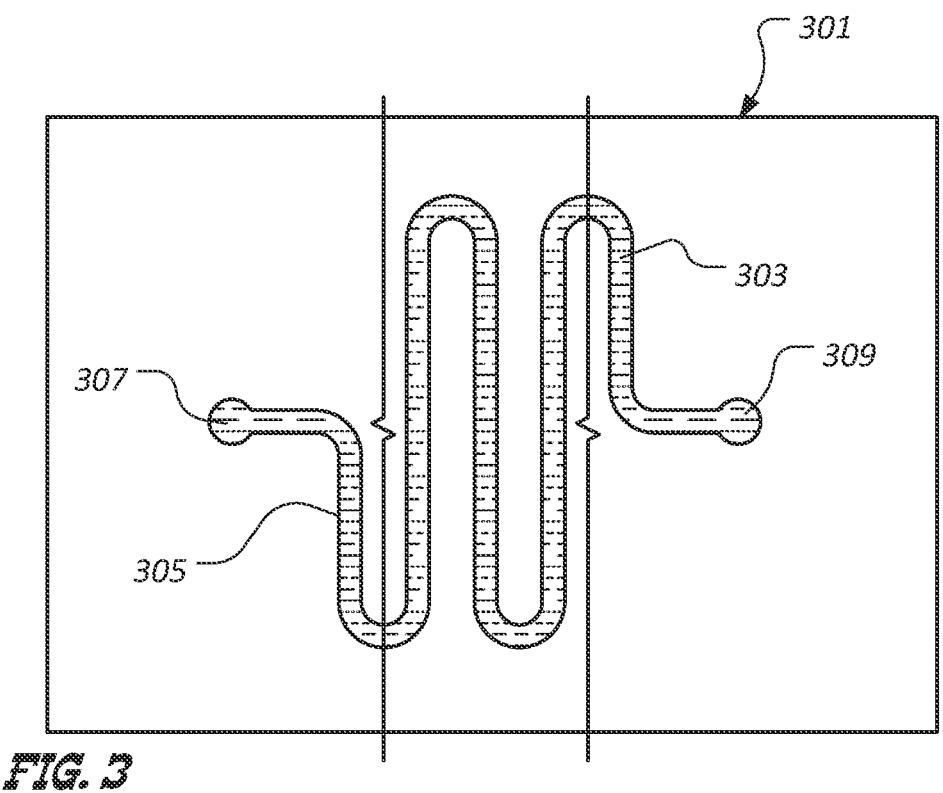
FIGS. 3 and 4 are stylized representations of a portion of an illustrative embodiment of a microfluidic device, such as the microfluidic device embodiment of FIG. 1.
Figure 4:
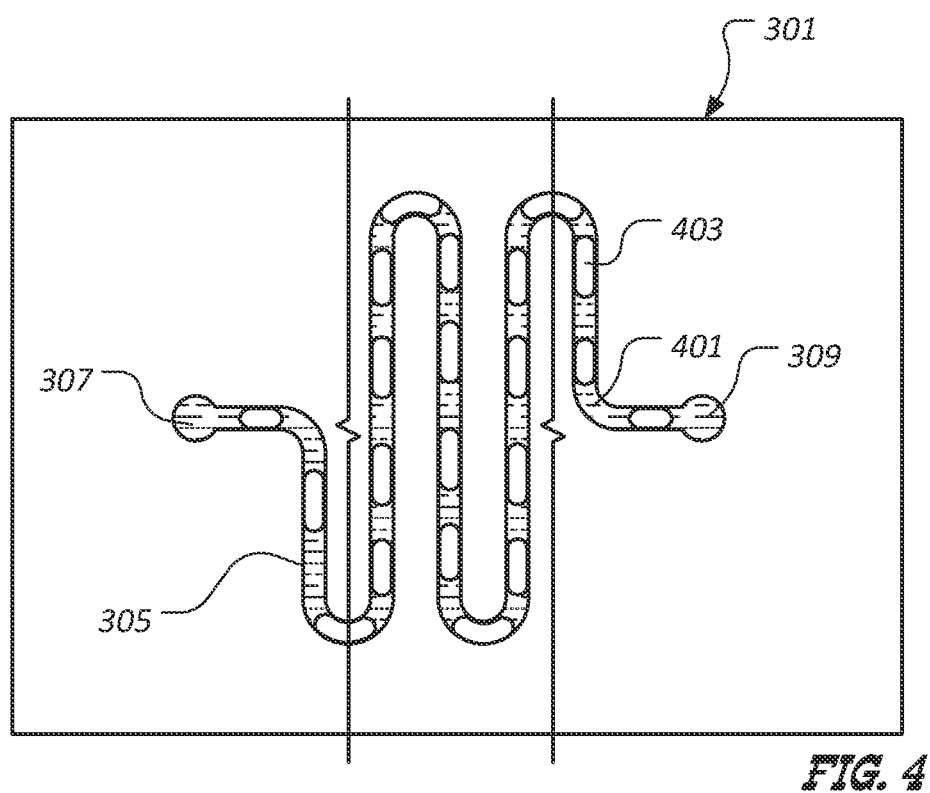

FIGS. 3 and 4 provide a stylized representation of a portion of a microfluidic device 301, such as microfluidic device 101, while in operation to hydrostatically measure phase behavior in a sample fluid. Referring in particular to FIG. 3, a sample fluid 303 is injected into a microchannel 305 of microfluidic device 301 via an entrance passageway 307 thereof. Pressure within microchannel 305 is maintained above the saturation pressure of sample fluid 303 and, in one embodiment, a differential pressure is maintained between entrance passageway 307 and an exit passageway 309 of microfluidic device 301 to generate a small flow of sample fluid 303 through microchannel 305. As shown in FIG. 3, sample fluid 303 substantially fills microchannel 305 and exists in substantially a single phase at the illustrated point in the process. After microchannel 305 is substantially filled with sample fluid 303, pressure is reduced at entrance passageway 307 and at exit passageway 309 until the pressure of sample fluid 303 reaches its saturation pressure, thus allowing sample fluid 303 to form a first phase 401, e.g., a liquid phase, and a second phase 403, e.g., a gas phase, in microchannel 305, such as shown in FIG. 4. In one embodiment, the appearance of second phase 403 is detected by optical methods, due to the differences in refractive indices of the first phase/glass interface and the second phase/glass interface. When second phase 403 appears, pressure is substantially held for a period of time, such as, for example five to ten minutes, to allow the phase distribution of sample fluid 303 to become generally uniform. After the phase distribution of sample fluid 303 is determined, the pressure of sample fluid 303 is iteratively, stepwise decreased, held to allow the phase distribution of sample fluid 303 to become generally uniform, and the distribution of sample fluid 303 is determined. In each iteration, the distribution of phases in sample fluid 303 is determined by optical means in one embodiment. These operations are conducted at substantially a constant temperature. The phase distribution, i.e., the volume of first phase 401 compared to the volume of second phase 403, can be correlated, for example, plotted on a graph, to show the relationship between pressure and phase volume fraction, such as liquid volume fraction.

Figure 5:
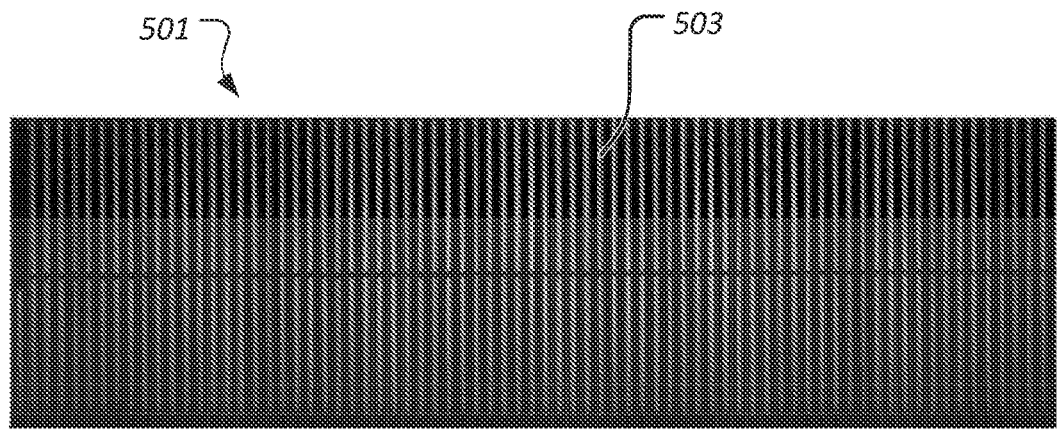
FIGS. 5-8 are photographic images of a sample fluid at various pressures disposed in a microfluidic device, such as the microfluidic device embodiment of FIG. 1.
Figure 6:
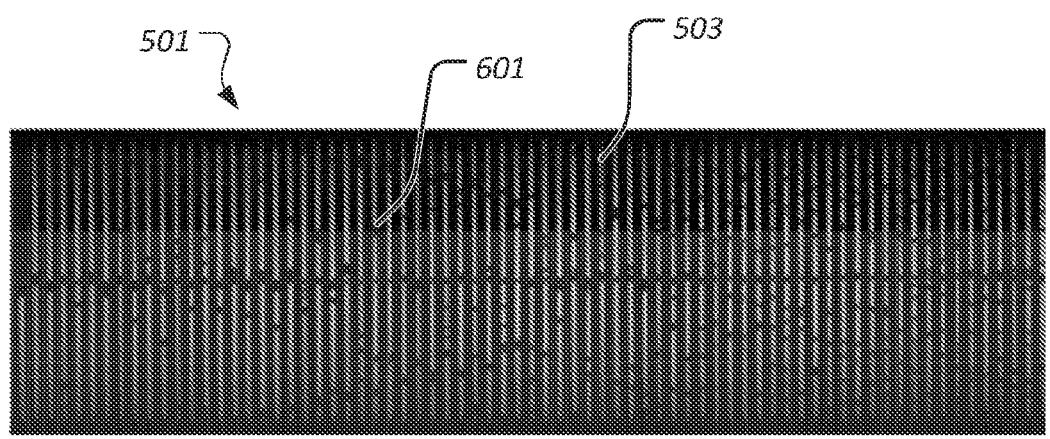
Figure 7:
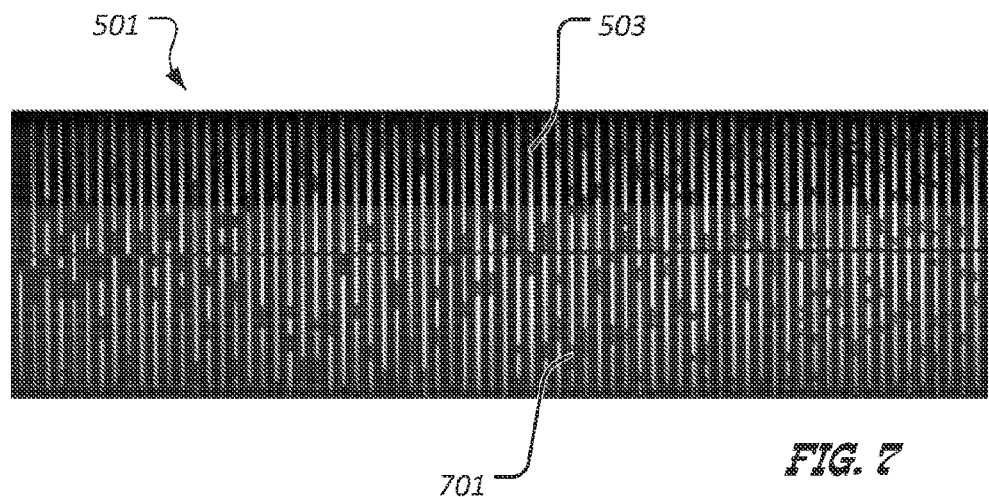
Figure 8:
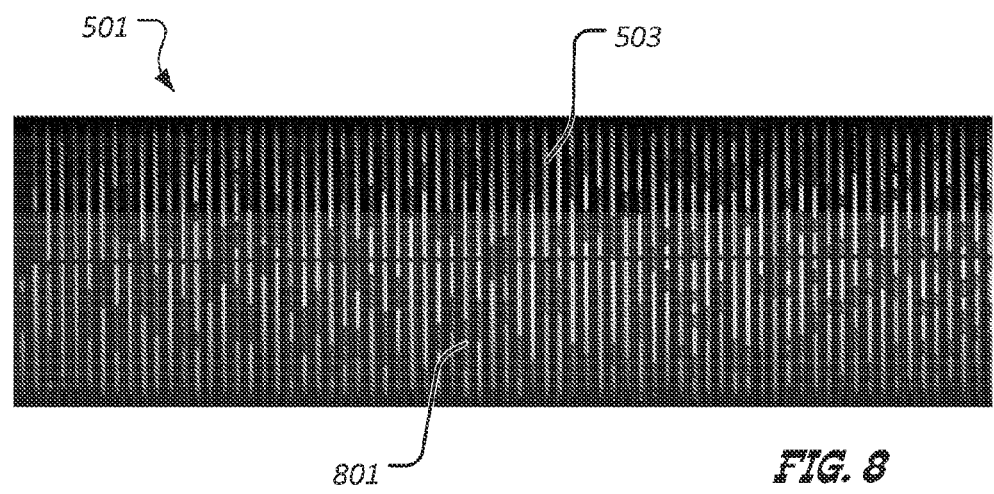

For example, FIGS. 5-8 are photographic images taken of a microfluidic device 501, such as microfluidic device 101 or 301, in which a black oil sample 503, exhibiting a gas/oil ratio of about 1509 standard cubic feet per stock tank barrel and an American Petroleum Institute (API) gravity of about 44.3 is disposed in the microchannel, such as microchannel 105 or 305, of microfluidic device 501. In FIG. 5, black oil sample 503 exists at a pressure above the saturation pressure of sample 503, for example, about 3664 pounds per square inch gauge at a substantially constant temperature of about 75° C. Accordingly, black oil sample 503 appears homogeneous and gray in color in the photograph. In FIG. 6, the pressure of black oil sample 503 is reduced below the saturation point of sample 503, allowing gas bubbles 601 (only one labeled for clarity) to form in the microchannel. Note that gas bubbles 601 appear darker than the remainder of black oil sample 503. In FIGS. 7 and 8, the pressure of black oil sample 503 is further decreased, allowing a greater volume of gas bubbles 701 and 801 (only one labeled in each of FIGS. 7 and 8 for clarity) to form in the microchannel.

Figure 9:
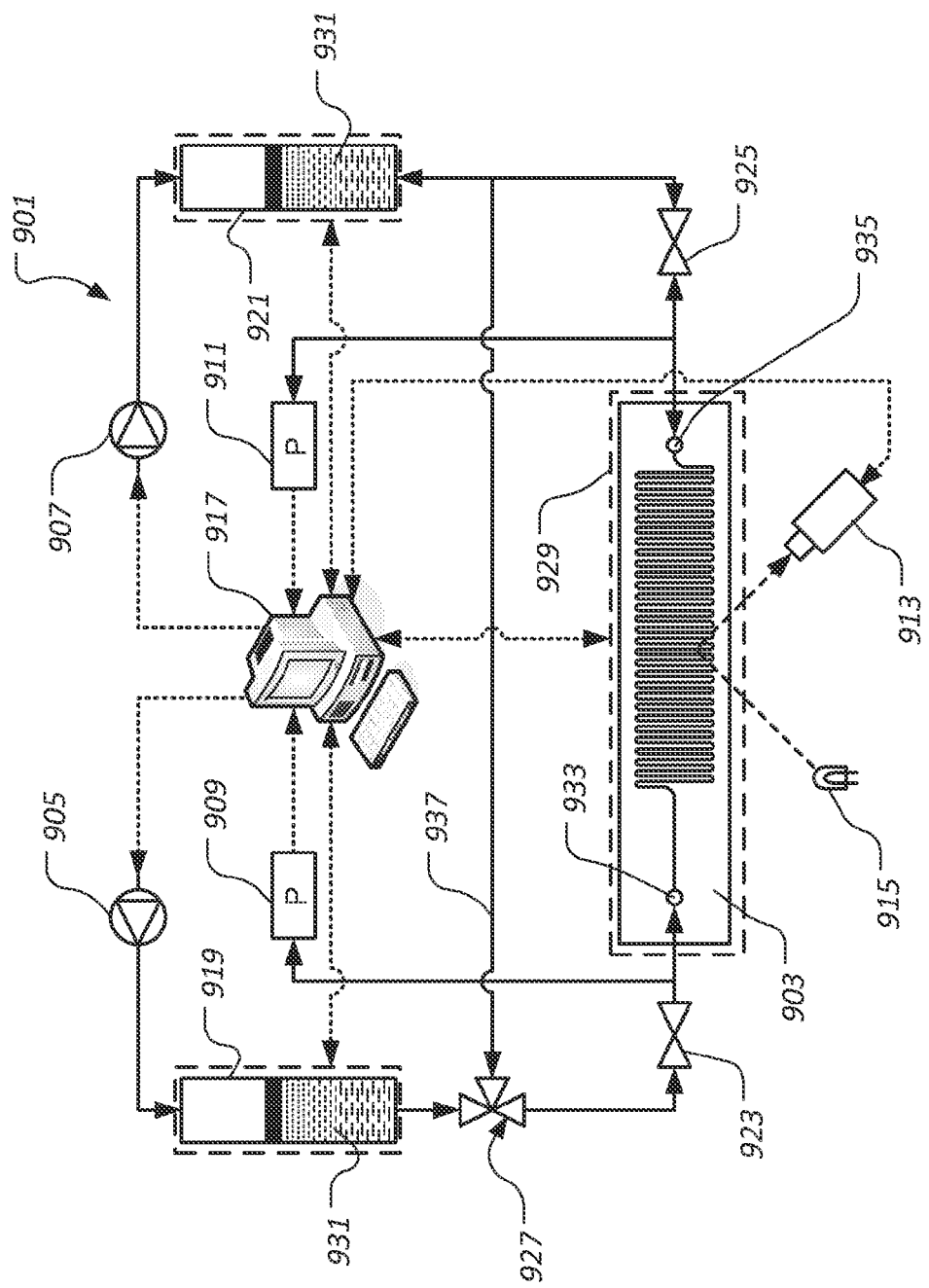
FIG. 9 is a schematic representation of an illustrative embodiment of a system incorporating a microfluidic device, such as the microfluidic device embodiment of FIG. 1, for measuring phase behavior of a fluid.

FIG. 9 depicts a schematic representation of an illustrative embodiment of a system 901 for measuring phase behavior of a fluid. In the illustrated embodiment, system 901 comprises a microfluidic device 903, such as microfluidic device 101 or 301; a first pump 905 and a second pump 907, such as high pressure syringe pumps marketed by Teledyne Isco of Lincoln, Nebr., USA; an inlet pressure sensor 909 and an outlet pressure sensor 911, such as pressure sensors marketed by Sensotreme GmbH of Ramsen, Germany; a camera 913, such as cameras marketed by Basler AG of Ahrensburg, Germany; a light source 915; and a computer 917. System 901, in the illustrated embodiment, further comprises a first sample container 919; a second sample container 921; a microfluidic device inlet valve 923; a microfluidic device outlet valve 925; an input switching valve 927; and a temperature control unit 929, such as ovens marketed by Sheldon Manufacturing of Cornelius, Oreg., USA. First sample container 919 and second sample container 921 contain portions of a sample fluid 931. First sample container 919 is in fluid communication with an entrance passageway 933 of microfluidic device 903 via input switching valve 927 and microfluidic device inlet valve 923. Second sample container 921 is in fluid communication with an exit passageway 935 of microfluidic device 903 via microfluidic device outlet valve 925. Second sample container 921 is also in fluid communication with input switching valve 927. Inlet pressure sensor 909 is operatively associated with entrance passageway 933 of microfluidic device 903 to measure the pressure of sample fluid 931 entering entrance passageway 933. Outlet pressure sensor 911 is operatively associated with exit passageway 935 of microfluidic device 903 to measure the pressure of sample fluid 931 exiting exit passageway 935. Both inlet pressure sensor 909 and outlet pressure sensor 911 are in communication with computer 917 to transmit pressure information to computer 917. First pump 905 is operatively associated with first sample container 919 to urge sample fluid 931 from sample container 919, through microfluidic device 903, and into second sample container 921. Second pump 907 is operatively associated with second sample container 921 to maintain a desired pressure within microfluidic device 903. Both first pump 905 and second pump 907 are in communication with computer 917 to allow computer 917 to control first pump 905 and second pump 907. Light source 915 is disposed to allow light propagating therefrom to fall onto microfluidic device 903. Camera 913 is disposed to capture images of microfluidic device 903, so that phase distributions of sample fluid 931 disposed in microfluidic device 903 can be determined. Camera 913 is in communication with computer 917 to transmit image information to computer 917. Microfluidic device 903 is operably associated with temperature control unit 929, such as a heating cell, to control the temperature of microfluidic device 903. It should be noted that, in some embodiments, camera 913 and light source 915 are omitted in favor of other techniques for determining the phase distributions of sample fluid 931.

In one illustrative use of system 901, sample fluid 931 is introduced from first sample container 919 into microfluidic device 903 via input switching valve 927 and microfluidic device inlet valve 923, while input switching valve 927 inhibits the flow of sample fluid 931 through a bypass line 937. The pressure of sample fluid 931 in second sample container 921 into microfluidic device 903 via microfluidic device outlet valve 925 is initially maintained substantially equivalent to the pressure of sample fluid 931 in first sample container 919. The pressure of sample fluid 931 in second sample container 921 is slowly reduced until microfluidic device 903 is substantially filled with sample fluid 931 at a single phase. With microfluidic device 903 substantially filled with sample fluid 931, input switching valve 927 is reconfigured to shut off flow of sample fluid 931 from first sample container 919 to entrance passageway 933 of microfluidic device 903 and allow flow of sample fluid 931 via bypass line 937. Pressure within microfluidic device 903 is controlled by second pump 907, as first pump 905 is isolated from microfluidic device 903. The pressure in microfluidic device 903 is slowly reduced until a second phase appears in sample fluid 931 disposed in microfluidic device 903. Camera 913 captures an image of microfluidic device 903 and transmits the image to computer 917, wherein a distribution of the phases is determined. Note that if sample fluid 931 is an oil, such as a black oil or heavy oil, the first phase is a liquid phase and the second phase is a gaseous phase. If sample fluid 931 is a gas condensate, the first phase is a gaseous phase and the second phase is a liquid phase that condenses on the walls of microfluidic device 903.

Figure 10:
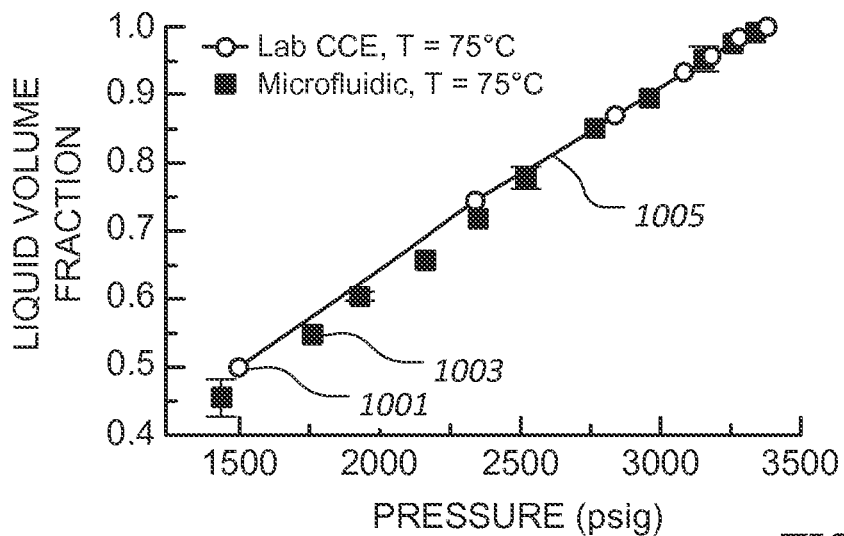
FIGS. 10 and 11 are graphical representations of examples of measurements of liquid volume fraction versus pressure for a black oil at about 75° C. and at about 125° C., respectively.
Figure 11:
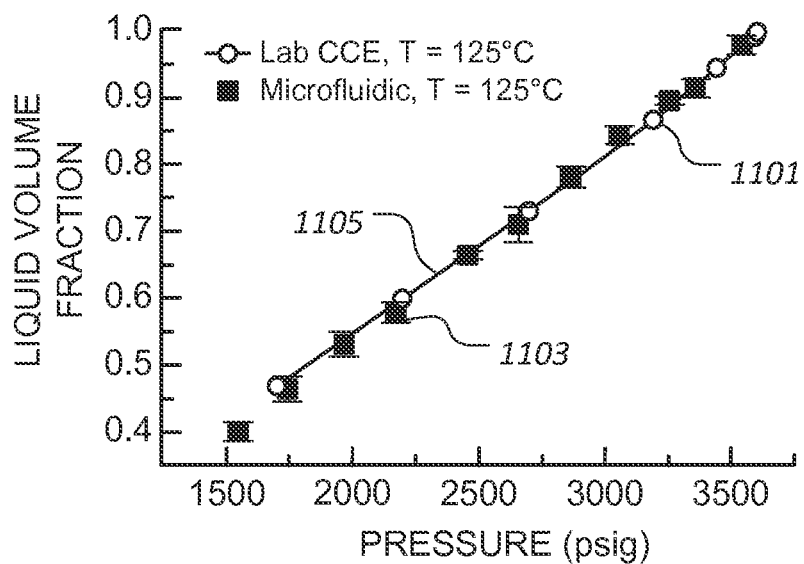

FIGS. 10 and 11 depict graphical representations of examples of measurements of liquid volume fraction versus pressure for a black oil at about 75° C. (FIG. 10) and at about 125° C. (FIG. 11). In each illustration, circles, such as circles 1001 and 1101, represent data points derived by a conventional constant composition expansion (CCE) pressure-volume-temperature technique. Squares, such as squares 1003 and 1103, represent data points derived using a microfluidic technique encompassed by the disclosed subject matter of the present application. A line 1005 in FIG. 10 and a line 1105 in FIG. 11 represent predictions from one or more tuned equation-of-state models based at least in part on the data derived by the conventional pressure-volume-temperature technique. As can be seen in FIGS. 10 and 11, data derived using the microfluidic technique correlates well with the data derived using the conventional pressure-volume-temperature technique at each temperature. In the depicted experiment for each temperature, less than an hour was required to derive data using the microfluidic technique, thereby allowing repeatability of the measurements, whereas conventional techniques to derive corresponding information typically require about a day per temperature to perform and are therefore not practically repeatable. Moreover, the setup used to perform the microfluidic technique used a few milliliters of reservoir fluid, as compared to conventional techniques that typically require about 50 milliliters of reservoir fluid. Smaller sample sizes result in safer operating conditions for personnel.

Figure 12:
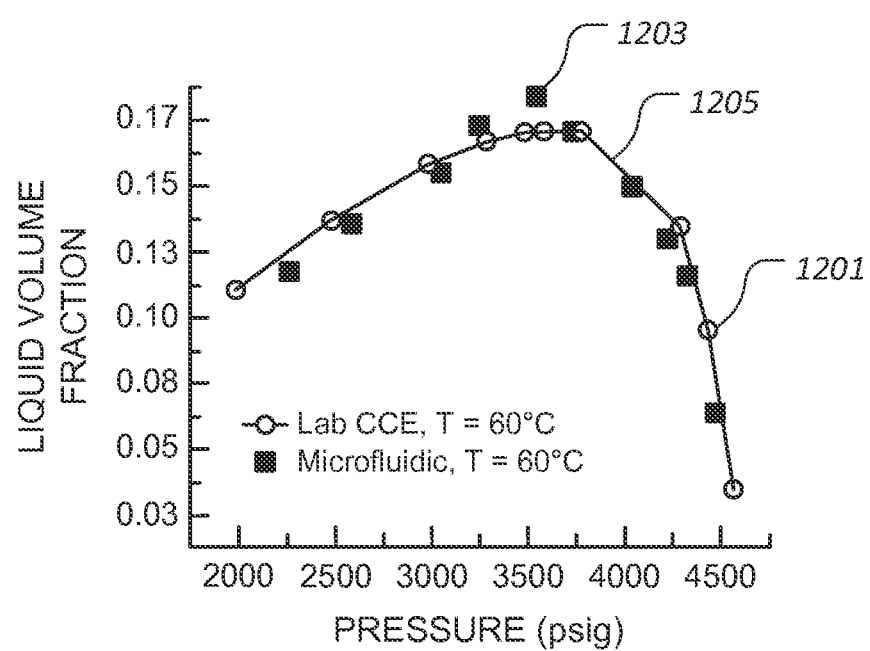
FIG. 12 is a graphical representation of an example of measurements of liquid volume fraction versus pressure for a synthetic gas condensate sample.

FIG. 12 depicts the results of a particular test of liquid phase volume as a function of pressure for a retrograde condensate comparing measurements obtained using a conventional CCE technique and measurements obtained using the microfluidic technique. In the illustration, circles, such as circle 1201, represent data points derived by a conventional CCE pressure-volume-temperature technique. Squares, such as square 1203, represent data points derived using a microfluidic technique encompassed by the disclosed subject matter of the present application. A line 1205 represents predictions from one or more tuned equation-of-state models based at least in part on the data derived by the conventional CCE pressure-volume-temperature technique. Excellent agreement between microfluidic and conventional measurements is evident throughout the depicted pressure range. In the test results shown in FIG. 12, the maximum absolute error of microfluidic measurements from conventional measurements is within two percent.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. An apparatus for measuring phase behavior of a reservoir fluid, comprising:
   a microfluidic device defining an entrance passageway, an exit passageway, and a microchannel in fluid communication with the entrance passageway and the exit passageway;
   a first sample container;
   a first pump operably associated with the first sample container;
   a second sample container;
   a second pump operably associated with the second sample container;
   an outlet valve fluidly coupled between the exit passageway of the microfluidic device and the second sample container;
   a bypass line in fluid communication with the second sample container; and
   an input switching valve fluidly coupled to the first sample container, the bypass line and the entrance passageway of the microfluidic device, wherein the input switching valve has a first configuration where reservoir fluid disposed in the first sample container is introduced from the first sample container into the entrance passageway of the microfluidic device while inhibiting the flow of the reservoir fluid through the bypass line, and wherein the input switching valve has a second configuration where reservoir fluid flows through the bypass line to the entrance passageway of the microfluidic device while reservoir fluid disposed in the first sample container does not flow into the entrance passageway of the microfluidic device;
   wherein the first pump and the first configuration of the input switching valve are used to urge reservoir fluid disposed in the first sample container into the entrance passageway of the microfluidic device; and
   wherein the second pump and the second configuration of the input switching valve are used to maintain a desired pressure within the microchannel of the microfluidic device.

2. The apparatus of claim 1, wherein the microfluidic device comprises:
   a first substrate defining the microchannel, an entrance well, and an exit well, the microchannel extending between and in fluid communication with the entrance well and the exit well; and
   a second substrate attached to the first substrate to form the microfluidic device, the second substrate defining the entrance passageway in fluid communication with the entrance well and the exit passageway in fluid communication with the exit well.

3. The apparatus of claim 1, further comprising:
   an inlet pressure sensor configured to measure a pressure of the reservoir fluid urged into the entrance passageway of the microfluidic device; and
   an outlet pressure sensor configured to measure a pressure of the reservoir fluid in the exit passageway of the microfluidic device.

4. The apparatus of claim 1, further comprising a computer for operating the first pump and the second pump based at least upon a pressure of the reservoir fluid urged into the entrance passageway of the microfluidic device and a pressure of the reservoir fluid urged into the exit passageway of the microfluidic device.

5. The apparatus of claim 1, further comprising a camera operably associated with the microfluidic device.

6. The apparatus of claim 1, wherein:
   the bypass line is fluidly coupled between the outlet valve and the input switching valve.

7. The apparatus of claim 1, further comprising:
   an inlet pressure sensor operably associated with the entrance passageway of the microfluidic device;
   an outlet pressure sensor operably associated with the exit passageway of the microfluidic device;
   a camera operably associated with the microfluidic device; and
   a computer operably associated with the first pump, the inlet pressure sensor, the second pump, and the outlet pressure sensor for operating the first pump and the second pump to provide a desired pressure drop across the microchannel of the microfluidic device.

8. The apparatus of claim 7, wherein the computer is operably associated with the camera for analyzing images of the microfluidic device.

9. The apparatus of claim 7, further comprising a light source for illuminating the microfluidic device.

10. The apparatus of claim 7, wherein:
    the first pump and the first configuration of the input switching valve are used to inject a reservoir fluid into a microchannel of a microfluidic device at a pressure resulting in a substantially single phase in the reservoir fluid;
    the second pump and the second configuration of the input switching valve are used to lower the pressure of the reservoir fluid in the microchannel until a second phase forms in the reservoir fluid; and
    the camera and the computer are used to determine a distribution of the phases of the reservoir fluid in the microchannel.

11. The apparatus of claim 10, wherein both the first pump and the second pump are operated to inject the reservoir fluid into the microchannel of the microfluidic device.

12. The apparatus of claim 11, wherein the operations of the first pump and the second pump are controlled by a computer.

13. The apparatus of claim 11, wherein the operations of the first pump and the second pump are controlled by using the inlet pressure sensor to monitor pressure of the reservoir fluid proximate the entrance passageway of the microfluidic device and by using the outlet pressure sensor to monitor pressure of the reservoir fluid proximate the exit passageway of the microfluidic device.

14. The apparatus of claim 10, wherein the camera is configured to produce an image of the reservoir fluid in the microchannel.

15. The apparatus of claim 14, wherein the computer is configured to analyze the image of the reservoir fluid in order to determine distribution of the phases of the reservoir fluid in the microchannel.

16. The apparatus of claim 14, further comprising a light source that illuminates the microfluidic device.

17. The apparatus of claim 10, wherein:
the second pump and the second configuration of the input switching valve are used to iteratively lower pressure of the reservoir fluid in the microchannel in predetermined steps; and
the camera and the computer are used to determine distribution of the phases of the reservoir fluid in the microchannel for each iteration.

18. The apparatus of claim 10, wherein:
with the input switching valve in its second configuration, pressure of the reservoir fluid in the microfluidic device is controlled by operation of the second pump.

19. The apparatus of claim 10, wherein:
the reservoir fluid is an oil, and the second phase is a gaseous phase.

20. The apparatus of claim 10, wherein:
the reservoir fluid is a gas condensate, and the second phase is a liquid phase.

* * * * *